United States Patent [19]

Bainville et al.

[11] Patent Number: 5,674,294
[45] Date of Patent: Oct. 7, 1997

[54] INTERVERTEBRAL DISK PROSTHESIS

[75] Inventors: Daniel Bainville, St. Avertin; François Laval, Monts; Raymond Roy-Camille, deceased, late of Paris, by Chantal Roy-Camille, legal representative; Gérard Saillant, La Celle St Cloud; François Lavaste, St Michel sur Orges, all of France

[73] Assignees: Commissariat a l'Energie Atomique; Universite Pierre et Marie Curie (Paris VI), both of France

[21] Appl. No.: 306,158

[22] Filed: Sep. 14, 1994

[30] Foreign Application Priority Data

Sep. 14, 1993 [FR] France .................................. 93 10917

[51] Int. Cl.⁶ ................................................. A61F 2/44
[52] U.S. Cl. .......................................................... 623/17
[58] Field of Search .................................. 623/16, 17, 18, 623/66

[56] References Cited

U.S. PATENT DOCUMENTS

| 3,867,728 | 2/1975 | Stubstad | 623/17 |
| 4,309,777 | 1/1982 | Patil | 623/17 |
| 4,874,389 | 10/1989 | Downey | 623/17 |
| 4,911,718 | 3/1990 | Lee et al. | 623/17 |
| 4,932,969 | 6/1990 | Frey et al. | 623/17 |
| 5,002,576 | 3/1991 | Fuhrmann et al. | 623/17 |
| 5,123,926 | 6/1992 | Pisharodi | 623/17 |

FOREIGN PATENT DOCUMENTS

| 0277282 | 10/1987 | European Pat. Off. | A61F 2/44 |
| 0346269 | 6/1989 | European Pat. Off. | A61F 2/44 |
| 0356112 | 8/1989 | European Pat. Off. | A61F 2/44 |
| 0610837 | 8/1994 | European Pat. Off. | 623/17 |
| 2263842 | 12/1972 | Germany | A61F 1/00 |
| 9000094 | 3/1991 | Germany | A61F 2/44 |

*Primary Examiner*—David J. Isabella
*Attorney, Agent, or Firm*—Hayes, Soloway, Hennessey, Grossman & Hage, P.C.

[57] ABSTRACT

A disk prosthesis for replacing a damaged spinal disk has two metal half-envelopes which confine between them a compression cushion having a controlled differential compression. The structure employs a membrane or diaphragm surrounding the compression cushion in order to insure a seal between the cushion and the environment and also has an anti-expulsion system for shaping the compression cushion in order to limit the expansion of the cushion out of the volume defined by the two metal cups and the membrane.

9 Claims, 1 Drawing Sheet

INTERVERTEBRAL DISK PROSTHESIS

TECHNICAL FIELD

The present invention relates to a prosthesis for replacing a damaged intervertebral disk of the vertebral column. It is used in the field of orthopedic surgery.

PRIOR ART

The vertebral column is constituted by a group of superimposed vertebrae interconnected by fibrocartilaginous disks, known as intervertebral disks. The latter have a fundamental function in the statics and dynamics of the vertebral column, ensuring the mobility between the different vertebrae.

Intervertebral disks are often subject to disorders linked with a compression of the vertebrae, a disk hernia, a displacement of the vertebrae or intervertebral degenerative arthritis. These disorders frequently give rise to pain or functional genes prejudicial to medical treatments and in certain cases can be of an invalidating nature.

The process used for relieving patients suffering from such disorders generally consists of surgery. Several surgical procedures are at present known.

The first method consists of a simple disk excision. The damaged area of the intervertebral disk is eliminated, which as a result eliminates the normal biomechanics of the disk. The two vertebrae adjacent to said disk then have a reduced reciprocal mobility. In addition, such an excision is not a final remedy to the patient's disorder and the deterioration of the disk can continue to evolve.

The second surgical method consists of an intervertebral arthrodesis by which the two vertebrae adjacent to the damaged disk are fused. This is a definitive remedy blocking arthrosis evolution, i.e. deterioration within the disk. The main disadvantage of this method is that it eliminates all disk mobility.

The third method and that which is most widely used at present consists of an intervertebral arthroplastic surgery for replacing the damaged disk by a prosthesis. Numerous disk prosthesis types are known and described in the work entitled "The Artificial Disc", published by Mario BROCK, H. Mickael MAYER and Klaus WEIGEL, SPRINGER-VERLAG 1991.

According to this work, the known disk prostheses can be placed in two major categories. These are prostheses for which the fibrous part of the natural disk is retained and used as a prosthesis envelope. The internal core of the natural disk is then replaced, either by a polymerizing product injected into the envelope, or by elastic parts introduced into the envelope, or by a bag inserted in the envelope and inflated by means of a liquid or a polymer. Such a prosthesis is more particularly described in U.S. Pat. No. 4 772 287 and EP-A-277 282. The main difficulty in obtaining such a prosthesis is that it is necessary to rediscover the geometry and compressive strength of the natural disk. Moreover, such a prosthesis cannot be looked upon as a definitive remedy for the patient, because the retained fibrous part of the disk may continue to deteriorate. The second category consists of entirely artificial prosthesis, which take the place of a completely removed natural disk.

A first procedure for producing these entirely artificial prostheses consists of introducing a sliding joint between the two vertebrae. This joint can be in direct contact with the vertebral plates. It can also consists of a centred swivel joint, as described in FR-A-2 372 622. Such a centred swivel joint prosthesis suffers from the disadvantage that the displacement of one vertebra with respect to another leads to friction at the swivel joint. Relatively rapidly such friction can give rise to irritation and after a certain time to migrating wear debris. Such debris can give rise to a foreign body reaction which, if it develops in contact with the medullary canal, can give rise to neurological disorders.

The second process for producing entirely artificial prostheses consists of using a deformable architecture rigidly connected to adjacent vertebral plates. Such a prosthesis is e.g. described in FR-A-2 124 815. This prosthesis more specifically comprises an element having the shape of an intervertebral disk and made from an elastomer material of the silicone type. It suffers from the disadvantage of only ensuring a limited mobility of the adjacent vertebrae, it having a relatively limited capacity to deform. This prosthesis also fails to prevent the radial expansion of the elastomer material during stresses exerted on the prosthesis, so that there is a risk of expulsion to the medullary canal.

BRIEF DESCRIPTION OF THE INVENTION

The present invention aims at obviating these disadvantages by proposing a disk prosthesis having two half-envelopes rigidly fixed to the vertebrae and connected by means of a compressible cushion able to absorb the deformations.

More specifically, the invention relates to a preshaped prosthesis for replacing a deteriorated intervertebral disk without friction or sliding. This prosthesis comprises two rigid half-envelopes shaped like cups and each cup being integrally fixed to one of the two vertebrae adjacent to the intervertebral disk to be replaced. A flexible means is positioned between the two half-envelopes and incorporates a compression cushion for absorbing deformations resulting from a displacement of one of the adjacent vertebrae with respect to the other. The compression cushion has at least two layers of materials having different rigidities. At least one of these two materials is volume compressible so as to elastically absorb the deformations of the adjacent material layer. An anti-expulsion system bordering the compression cushion completes the structure.

In a preferred form of the invention, the materials forming the compression cushion are fixed to the half-envelopes by adhesion and by means of substantially circular, radial ribs.

The prosthesis according to the invention has a membrane or diaphragm fixed to each of the half-envelopes and surrounding the compression cushion in order to ensure a seal between said cushion and the environment. Advantageously, the anti-expulsion system has annular means for shaping the compression cushion in order to limit the expansion of said cushion out of the volume defined by the two half-envelopes.

BRIEF DESCRIPTION OF THE DRAWINGS

FIG. 4 is a sectional view of still another embodiment of the disk prosthesis according to the invention.

DETAILED DESCRIPTION OF THE EMBODIMENTS

Figure 1:
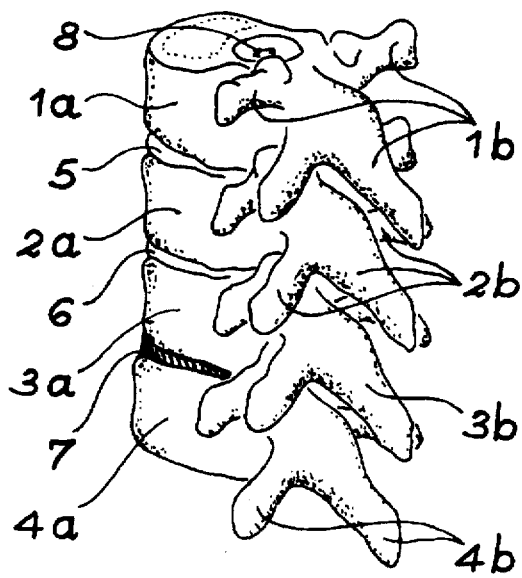
FIG. 1 is a general, perspective view of a portion of the vertebral column showing the location of a disk prosthesis according to the invention.

FIG. 1 shows a vertebral column portion having four vertebrae 1, 2, 3, 4 interconnected by intervertebral disks.

According to the embodiment shown in FIG. 1, the vertebrae 1, 2 and the vertebrae 2, 3 are respectively connected by the intervertebral disk 5, 6. In this case, the vertebrae 3, 4 are connected by a disk prosthesis 7, which is shown in hatched form in FIG. 1. FIG. 1 shows the vertebral foramen 8 filled by the spinal cord. It is also possible to see on each vertebra 1, 2, 3, 4, the vertebral body, respectively 1a, 2a, 3a, 4a, as well as the apophyses 1b, 2b, 3b, 4b.

Like the intervertebral disks 5, 6, the disk prosthesis 7 has an external "bean" shape and is positioned between the vertebral bodies 3a, 4a of the vertebrae 3 and 4.

Figure 2:
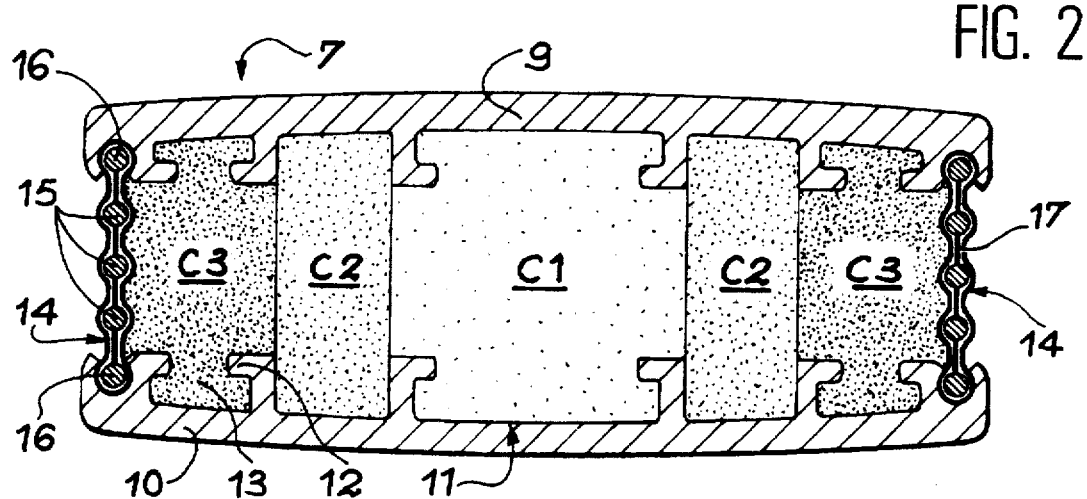
FIG. 2 shows in a sectional view one preferred embodiment of the disk prosthesis according to the invention.

FIG. 2 is a sectional view of a first embodiment of the disk prosthesis 7, which has two cup-shaped half-envelopes 9, 10. These cups 9, 10 are metallic and each is fixed to the vertebral body of one of the two adjacent vertebrae. They can e.g. be made from an alloyed titanium or from chromium molybdenum alloy.

According to the embodiment of FIG. 1, the cup 9 is fixed to the body 3a of the vertebra 3 and the cup 10 to the body 4a of the vertebra 4. Each of these cups 9, 10 is in contact, by its convex wall, with one of the adjacent vertebrae, the concave walls of the cups 9, 10 facing one another. Thus, the disk prosthesis 7 in overall manner reproduces the shape of the intervertebral disk which it replaces.

The fixing of the metal cups 9, 10 to the adjacent vertebrae can take place by standard orthopedic surgery methods, namely fixing by screwing or by using pins. This fixing can also take place by means of cement, by rehabitation by the tissues of the specially treated surface (hydroxyapatite) or by a combination of these processes. No matter what connecting method is adopted, said connection is rigid and joins each cup 9, 10 to one of the adjacent vertebrae.

Between said cups 9, 10 are introduced flexible means consisting of a compression cushion 11 formed from several layers of materials having different compressibility coefficients. According to a preferred embodiment of the invention, said materials are polymers able to adhere to the concave wall of each cup.

According to this preferred embodiment of the invention, the concave wall of each cup 9, 10 has circular ribs 12 which extend radially with respect to the cups and form between them, grooves 13 into which partly penetrates a multi element compression cushion 11. The said ribs 12 maintain the compression cushion in the volume defined by the two cups 9, 10.

Radial ribs can also make it possible to limit the relative rotation of the cups 9, 10 by means of the compression cushion 11. Moreover, the concave walls of the cups 9, 10 can previously undergo treatments able to increase the adhesion capacity of the polymers of the cushion to the metal of the cups 9, 10.

According to the embodiment shown in FIG. 2, the multi element cushion 11 incorporates three layers of polymers which can either be moulded in situ between the two cups, or joined between the cups. These polymers preferably have different compressibility coefficients (i.e. different rigidities) and are distributed so as to obtain the desired prosthesis flexibility. More specifically, said flexibility is dependent on the mechanical characteristics (modulus of elasticity, volume compressibility, etc.) of the polymers used and the arrangement of the polymer layers.

The polymer layers constituting the cushion 11 can be arranged so as to form superimposed, substantially planar layers parallel to the plane of the cups 9, 10 (see FIG. 4).

According to the embodiment shown in FIG. 2, the layers of polymers are arranged so as to be concentric and perpendicular to the plane of the cups. In known manner, the function of the disk to be replaced varies according to its location in the vertebral column. A disk of lumbar vertebrae has functions differing from those of a disk of the dorsal vertebrae or cervical vertebrae. Thus, the disk prosthesis according to the invention reproduces these different functions by varying the overall modulus of elasticity of the prosthesis. To do this, different arrangements of the polymer layers can be used:
- an arrangement such that the overall modulus of elasticity increases from the centre of the prosthesis towards the outside,
- an arrangement such that the overall modulus of elasticity decreases from the centre of the prosthesis to the outside,
- an arrangement such that the overall modulus of elasticity is alternately increasing and decreasing.

According to the embodiment of FIG. 2, the layers of polymers of the cushion 11 are arranged concentrically to one another. The "core" layer C1, which is the most central layer of the cushion 11, is made from a polymer which is only slightly volume compressible. The central layer C2, i.e. that adjacent to the core layer G1, is made from a filled polymer, which is compressible in volume and therefore able to absorb deformations undergone by the adjacent layers. The outermost layer C3 in the embodiment of FIG. 2 is made from a polymer which is only slightly volume compressible.

According to the invention, a membrane or diaphragm 14 surrounds the compression cushion 11 on its periphery, thus providing a tight barrier for preventing any migration of particles of compressible materials from the cushion 11 to the outside of the prosthesis. In FIG. 2, said membrane 14 is concentric to the layers C1, C2 and C3.

According to an embodiment, said membrane 14 is a polyethylene film.

The membrane can also assume the form of a bellows, thus making it possible to improve the fatigue strength during bending movements.

The membrane 14 is fixed on either side to the cups 9 and 10 in order to seal the cushion. Such a tightness of the cushion 11 and therefore the prosthesis limits the transfer to the organism of particles resulting from fatigue of the materials of the cushion 11. This ensures a better tolerance of the prosthesis by the organism and therefore a longer implantation period.

According to the invention, the flexible means also incorporate annular means for shaping the cushion 11. These annular means are radially rigid and ensure that there is no radial expansion of the materials of the cushion 11 outside the volume defined by the cups 9 and 10. These annular means ensure an identical geometry of the prosthesis, no matter what deformations are suffered by the cushion 11. Therefore said annular means constitute an anti-expulsion system with respect to the medullary canal.

According to the embodiment shown in FIG. 2, said annular means comprise a plurality of metal rings 15 having a circular section and a shape adapted to the contour of the compression cushion. They also incorporate two metal rings 16 arranged on either side of the plurality of rings 15 and in contact with each of the cups 9, 10. These rings 16 can e.g. be crimped on the border of the cups 9, 10, so as to ensure the closing of the membrane 14 around the cushion 11.

According to the embodiment of FIG. 2, a lattice 17 maintains the rings 15 and the positioning of the rings 16 on the border of the cups. This lattice 17 is positioned substantially perpendicular to the plane of the cups 9, 10 and over the entire periphery of the cushion 11. This lattice can e.g. be made from nylon.

According to an embodiment of the invention, the membrane 14, the rings 16 and the lattice 17 can be integrated, namely the rings 16 and the lattice 17 by braiding and the membrane 14 by potting.

Figure 3:
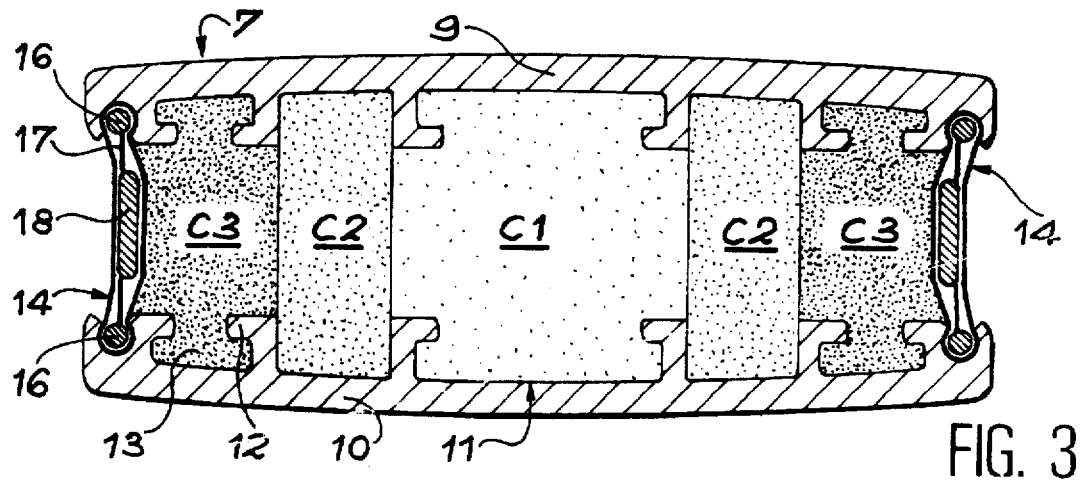
FIG. 3 is a sectional view of another embodiment of the disk prosthesis according to the invention.

FIG. 3 is a sectional view of a second embodiment of the disk prosthesis 7. As in the embodiment of the disk prosthesis shown in FIG. 2, the disk prosthesis 7 of FIG. 3 has:
- two cups 9, 10 with ribs 12 forming grooves 13,
- a compression cushion 11 having several polymer layers C1, C2, C3 with different compression capacities,
- a membrane 14 surrounding the cushion 11.

This disk prosthesis 7 also has annular means for shaping the cushion 11. According to this second embodiment, these annular means consist of a circular metal strip 18 having a shape adapted to the contour of the cushion 11 and connected to the two rings 16 by means of the lattice 17. This assembly of the strip 18, rings 16 and lattice 17 has an identical function to the annular means described in the first embodiment of the prosthesis according to FIG. 2.

According to a third embodiment of the invention illustrated in FIG. 4, the layers of materials forming the compression cushion are arranged approximately parallel to the plane of the half-envelopes. In this embodiment the membrane 14 and shaping means 15 are the same as in FIG. 2.

According to a fourth (unillustrated) embodiment of the disk prosthesis, the annular shaping means for the cushion consist of a wire or thread helically wound around the compression cushion. The advantage of this embodiment is that it is easy to implement. Moreover, these annular means permit a stability in the positioning of the individual turns, limits the relative rotation of the cup and contributes to the tensile and compressive strength of the prosthesis.

Thus, it is easily understandable that such a disk prosthesis permits movements of a vertebra with respect to its adjacent vertebra by deformation of the compression cushion 11, whilst sealing the prosthesis with respect to the organism. Therefore such a prosthesis limits the risk of the prosthesis being rejected by the organism.

We claim:

1. Preshaped prosthesis for replacing a deteriorated intervertebral disk without friction or sliding, comprising:
   two rigid half-envelopes shaped like cups, each half-envelope being adapted to be integrally fixed to one of two vertebrae adjacent to the intervertebral disk to be replaced,
   flexible means positioned between the two half-envelopes and incorporating a compression cushion having at least a central layer and an outer layer which are concentric and formed of materials having different relative rigidities, the central layer being deformable and relatively volume compressible for elastically absorbing the deformation of the outer layer which is deformable and only slightly volume compressible; and anti-expulsion means bordering the compression cushion for preventing the expansion of the outer layer beyond the volume defined by the two half-envelopes, the deformation of the outer layer being absorbed by the central layer.

2. Prosthesis according to claim 1, wherein the materials constituting the compression cushion are fixed to the half-envelope by adhesion and ribs.

3. Prosthesis according to claim 1, and comprising a membrane fixed to each of the half-envelopes and surrounding the compression cushion in order to ensure the sealing thereof.

4. Prosthesis according to claim 1, wherein the anti-expulsion means comprises annular means for shaping the compression cushion.

5. Prosthesis according to claim 4, wherein the annular shaping means incorporate a plurality of rings each having a circular section and a shape adapted to the contour of the compression cushion and which are maintained together by a lattice means, two of the said rings being crimped on the border of the two half-envelopes so as to ensure a maximum distance between said half-envelopes.

6. Prosthesis according to claim 4, wherein the annular shaping means incorporate a strip having a shape adapted to the contour of the compression cushion and two rings each with a circular section, said rings being crimped on the border of the two half-envelopes and a lattice means connecting the strip to the rings and ensuring a maximum distance between said half-envelopes.

7. Prosthesis according to claim 4, wherein the annular shaping means incorporate a wire wound helically around the compression cushion.

8. Preshaped prosthesis for replacing a deteriorated intervertebral disk without friction or sliding, comprising:
   two rigid half-envelopes shaped like cups, each half-envelope being adapted to be integrally fixed to one of two vertebrae adjacent to the intervertebral disk to be replaced;
   flexible means positioned between the two half-envelopes and incorporating a compression cushion having at least two layers of materials having different relative rigidities for absorbing deformations resulting from a displacement of one of the adjacent vertebrae with respect to the other, at least one material layer being relatively volume compressible for elastically absorbing the deformations of the adjacent material layer; and anti-expulsion means incorporating annular means for shaping the compression cushion in order to limit the expansion of the latter out of the volume defined by the two half-envelopes, said annular means incorporating a plurality of metal rings each having a circular section and a shape adapted to the contour of the compression cushion and which are maintained together by a lattice means, two of the said metal rings being crimped on the border of the two half-envelopes so as to ensure a maximum distance between said half-envelopes, bordering the compression cushion.

9. Prosthesis according to claim 8, characterized in that the annular shaping means incorporate a metal strip having a shape adapted to the contour of the compression cushion, two metal rings each with a circular section and crimped on the border of the two half-envelopes, and a lattice means connecting the strip to the rings and ensuring a maximum distance between said half-envelopes.

* * * * *